(12) United States Patent
Sagardia et al.

(10) Patent No.: US 11,564,825 B2
(45) Date of Patent: Jan. 31, 2023

(54) LUMBAR-SUPPORTING BACK-BRACING APPARATUS AND METHODS

(71) Applicant: DJO, LLC, Vista, CA (US)

(72) Inventors: Beñat Sagardia, Saint-Pée-sur-Nivelle (FR); Julien Oxoteguy, Mouguerre (FR)

(73) Assignee: DJO, LLC, Carlsbad, CA (US)

( * ) Notice: Subject to any disclaimer, the term of this patent is extended or adjusted under 35 U.S.C. 154(b) by 0 days.

(21) Appl. No.: 17/172,536

(22) Filed: Feb. 10, 2021

(65) Prior Publication Data
US 2021/0244560 A1    Aug. 12, 2021

Related U.S. Application Data

(60) Provisional application No. 63/101,208, filed on Mar. 10, 2020, provisional application No. 62/975,298, filed on Feb. 12, 2020.

(51) Int. Cl.
*A61F 5/02* (2006.01)
*A61F 5/30* (2006.01)

(52) U.S. Cl.
CPC .............. *A61F 5/028* (2013.01); *A61F 5/30* (2013.01)

(58) Field of Classification Search
CPC .. A61F 5/00; A61F 5/01; A61F 5/0102; A61F 5/0104; A61F 5/02; A61F 5/022;
(Continued)

(56) References Cited

U.S. PATENT DOCUMENTS 2,955,293 A  *  10/1960  Peterson ................ A41B 13/10
                                                      2/48
4,080,962 A  *   3/1978  Berkeley ................ A61F 5/024
                                                      602/19
(Continued)

FOREIGN PATENT DOCUMENTS

| CN | 207886322 U | 9/2018 |
|---|---|---|
| FR | 1104562 A | 11/1955 |
| KR | 20120111830 A | 10/2012 |

OTHER PUBLICATIONS

United Medicare, Body Belts & Supports, https://www.unitedmedicareindia.in/body-back-support-belts-braces-manufacturers-india.html, accessed: Feb. 13, 2020.

*Primary Examiner* — Ophelia A Hawthorne
*Assistant Examiner* — Gina McCarthy
(74) *Attorney, Agent, or Firm* — Veros Legal Solutions, LLP

(57) ABSTRACT

A back-bracing apparatus and associated methods of use and/or manufacture are provided. The apparatus includes support and belt portions. The support portion includes a plurality of posterior ribs configured to abut and extend along a low back of a user and a bracing web component having a plurality of crossing structures coupling adjacent ribs. At least one rib includes first and second upper slots disposed at opposite sides of an upper portion of the rib and first and second lower slots disposed at opposite sides of a lower portion of the rib. The belt portion includes an inner strap coupled to the support portion and configured to wrap around a torso and a low back of the user, and upper and lower outer straps configured to pass through the first and second upper slots and the first and second lower slots, respectively, and wrap around the inner strap.

19 Claims, 9 Drawing Sheets

(58) Field of Classification Search
CPC .......... A61F 5/024; A61F 5/026; A61F 5/028; A61F 5/03; A61F 5/05; A61F 5/30; A61F 5/32; A61F 5/003; A61F 5/0193; A61H 1/006; A61H 1/008; A61H 2201/1623; A61H 2201/1626; A41B 13/10; A47H 23/10; D03D 15/56
See application file for complete search history.

(56) References Cited

U.S. PATENT DOCUMENTS

| | | | |
|---|---|---|---|
| 4,245,628 A * | 1/1981 | Eichler | A61F 5/028 602/19 |
| 4,976,257 A | 12/1990 | Akin et al. | |
| 5,363,863 A * | 11/1994 | Lelli | A61F 5/028 602/19 |
| 5,547,462 A | 8/1996 | Lanigan et al. | |
| 6,666,838 B2 | 12/2003 | Modglin et al. | |
| 9,119,975 B2 | 9/2015 | Hu et al. | |
| 2004/0077983 A1 | 4/2004 | Reinecke et al. | |
| 2004/0267293 A1* | 12/2004 | Byrum | A61F 5/003 606/157 |
| 2011/0034845 A1* | 2/2011 | Polliack | A61F 5/0193 602/19 |
| 2011/0295169 A1* | 12/2011 | Hendricks | A61F 5/028 602/19 |
| 2015/0328036 A1 | 11/2015 | Frangi et al. | |
| 2016/0045355 A1* | 2/2016 | Safko | A61F 5/028 602/19 |
| 2018/0160838 A1* | 6/2018 | Chen | A47H 23/10 |
| 2018/0369008 A1 | 12/2018 | Grim et al. | |
| 2019/0021895 A1* | 1/2019 | Breuil | D03D 15/56 |
| 2021/0113213 A1* | 4/2021 | Dahl | A61F 5/32 |

\* cited by examiner

1300 ⇾

1302 ⇾
Form a support portion by:

1304 ⇾
Forming a plurality of posterior ribs configured to abut and extend along a low back of a user by sandwiching rigid metallic stays between an outer layer comprising polyurethane overinjected onto textile and an inner layer comprising a soft, absorbant material, at least one rib of the plurality of posterior ribs comprising: a first upper slot disposed at a first upper side of the rib and a second upper slot disposed at a second upper side of the rib opposite the first upper side, and a first lower slot disposed at a first lower side of the rib and a second lower slot disposed at a second lower side of the rib opposite the first lower side, and 1306 ⇾
Forming a bracing web component comprising a plurality of crossing structures from at least the outer layer and the inner layer , wherein each rib of the plurality of posterior ribs is physically coupled to an adjacent rib of the plurality of posterior ribs by at least one of the crossing structures 1308 ⇾
Provide a belt portion by:

1310 ⇾
Forming an inner strap that is configured to be coupled to the support portion And to wrap around a torso and a low back of the user and thereby the apparatus to be secured around the torso of the user 1312 ⇾
Forming an upper outer strap that is configured to pass through the first and second upper slots of the at least one rib of the plurality of posterior ribs and to wrap around the inner strap, the torso and the low back of the user 1314 ⇾
Forming a lower outer strap that is configured to pass through the first and second lower slots of the at least one rib of the plurality of posterior ribs and to wrap around the inner strap, the torso and the low back of the user

FIG. 13

LUMBAR-SUPPORTING BACK-BRACING APPARATUS AND METHODS

CROSS-REFERENCE TO RELATED APPLICATIONS

This application claims priority to U.S. Provisional Application No. 62/975,298, filed on Feb. 12, 2020, and to U.S. Provisional Application No. 63/101,208, filed on Mar. 10, 2020, the entire contents of both applications are hereby incorporated by reference.

TECHNICAL FIELD

The present disclosure relates generally to back braces and, more particularly, to a back brace for supporting and stabilizing at least a lumbar region of a user.

BACKGROUND

The spine has five distinct areas: the cervical area comprising vertebrae C1 through C7, the chest area comprising the vertebrae T1 through T12, the lumbar region comprising the vertebrae L1 through L5, the sacrum comprising the vertebrae S1 through S5, and the coccyx comprising 3 to 5 fused vertebrae, the number of which varied by individual. Individuals can have back pain in any one or more of these regions. For low back pain, compression of the nerves servicing the vertebral discs can cause or promote radiating pain in the lower limbs. In such cases, low back pain is sometimes referred to as existing in the L4-L5, L5-S1 or L3 regions, locations or junctions.

Regarding low back pain, a distinction can be made between extremely frequent common low back pain and specific low back pain linked to a specific cause or indication (e.g., scoliosis, spondylitis, etc.), as well as by its duration. Common low back pain is most often mild, not causing major injury, and often disappears after a few weeks. Pain lasting less than approximately 4 weeks is sometimes referred to as "acute" low back pain. However, recurrences can be frequent and it may be desirable to prevent or treat acute low back pain lest it become "subacute" low back pain, defined by persistent debilitating pain lasting more than 4 weeks but less than 3 months, and eventually "chronic" low back pain, defined by persistent debilitating low back pain beyond 3 months.

Low back pain can also be described by its mode of appearance, e.g., during effort, movement, prolonged posture maintenance, driving, vibrations, and/or whether it is spontaneous or repetitive in nature.

According to a National Research and Safety Institute (INRS) report, the prevalence of low back pain is relatively high—more than 2 in 3 employees (e.g., 60-70%) have had, now have, or will have low back pain. And the average duration of work stoppages cause by such low back pain is approximately two months—a statistic that has almost tripled in the last 40 years. With the average duration of low back pain recognized as professional illness being one year, the average cost of such flow back pain is approximately 44,000 Euros per person affected and aggregates to 11.5 million workdays lost due to low back pain.

Multiple risk factors contribute to these relatively high rates of low back pain occurrence, including but not limited to manual handling, whole body vibration, hard physical work, stressful postures and falls, and some psychosocial risk factors. Such factors occur and/or otherwise exist in many trades and are central contributors to illness or long-term accidents, difficulties in returning to work and at least partly explain increased costs associated with low back pain. In fact, low back pain accounts for 20% of work accidents and 7% of occupational diseases.

Low back pain can also be experienced while carrying heavy loads or enduring whole-body vibrations. For example, handlers, machine operators expose workers to restrictive postures. If carrying such loads are made under poor conditions, risk of low back pain increases. Similarly, exposure to whole-body vibration characterizes many professions where workers use mobile machinery, e.g., construction machinery, handling trolleys, etc., or vibrating material. Such vibrations are transmitted to the whole body through the spine. The risk of injury depends on the intensity and frequency of the vibrations, with frequencies being most dangerous to the human body in the 2-10 Hz range. Besides the classical compression/stretching cycles caused by such vibrations, operators are often subject to continuous postural corrections.

Prevention or lessening exposure to such contributors to low back pain illustrates the need for both the reduction of risk for all individuals and for allowing those currently suffering from low back pain to operate within their lives without significant limitation as a result of low back pain. Numerous preventative measures can be implemented, including but not limited to reduction of exposure times to such contributing factors and/or proper selection of, and improvement in the operating conditions of, equipment while also utilizing a lumbar-supporting apparatus or brace that provides both shock absorption and spinal protection.

SUMMARY

A lumbar-supporting back-bracing apparatus is provided. The apparatus includes a support portion and a belt portion. The support portion includes a plurality of posterior ribs configured to abut and extend along a low back of a user. At least one rib of the plurality of posterior ribs includes a first upper slot disposed at a first upper side of the rib and a second upper slot disposed at a second upper side of the rib opposite the first upper side, and a first lower slot disposed at a first lower side of the rib and a second lower slot disposed at a second lower side of the rib opposite the first lower side. The support portion includes a bracing web component comprising a plurality of crossing structures, wherein each rib of the plurality of posterior ribs is physically coupled to an adjacent rib of the plurality of posterior ribs by at least one of the crossing structures. The belt portion includes an inner strap coupled to the support portion and configured to wrap around a torso and a low back of the user and thereby secure the apparatus around the torso of the user. The belt portion includes an upper outer strap configured to pass through the first and second upper slots of the at least one rib of the plurality of posterior ribs and wrap around around the inner strap, the torso and the low back of the user. The belt portion includes a lower outer strap configured to pass through the first and second lower slots of the at least one rib of the plurality of posterior ribs and wrap around around the inner strap, the torso and the low back of the user.

A method of manufacturing a lumbar-supporting back-bracing apparatus is provided. The method includes forming a support portion and providing a belt portion. Forming the support portion includes forming a plurality of posterior ribs configured to abut and extend along a low back of a user by sandwiching rigid metallic stays between an outer layer comprising polyurethane overinjected onto textile and an inner layer comprising a soft, absorbant material. At least one rib of the plurality of posterior ribs includes a first upper slot disposed at a first upper side of the rib and a second upper slot disposed at a second upper side of the rib opposite the first upper side, and a first lower slot disposed at a first lower side of the rib and a second lower slot disposed at a second lower side of the rib opposite the first lower side. Forming the support portion includes forming a bracing web component including a plurality of crossing structures from at least the outer layer and the inner layer. Each rib of the plurality of posterior ribs is physically coupled to an adjacent rib of the plurality of posterior ribs by at least one of the crossing structures. Providing the belt portion includes forming an inner strap that is configured to be coupled to the support portion and to wrap around a torso and a low back of the user and thereby the apparatus to be secured around the torso of the user. Providing the belt portion includes forming an upper outer strap that is configured to pass through the first and second upper slots of the at least one rib of the plurality of posterior ribs and to wrap around the inner strap, the torso and the low back of the user. Providing the belt portion includes forming a lower outer strap that is configured to pass through the first and second lower slots of the at least one rib of the plurality of posterior ribs and to wrap around the inner strap, the torso and the low back of the user.

A method of using a lumbar-supporting back-bracing apparatus is provided. The method includes disposing a plurality of posterior ribs of a support portion of the lumbar-supporting back-bracing apparatus against a low back of a user. At least one rib of the plurality of posterior ribs includes a first upper slot disposed at a first upper side of the rib and a second upper slot disposed at a second upper side of the rib opposite the first upper side, and a first lower slot disposed at a first lower side of the rib and a second lower slot disposed at a second lower side of the rib opposite the first lower side. The support portion further includes a bracing web component including a plurality of crossing structures. Each of the crossing structures physically couples two adjacent ribs of the plurality of posterior ribs. The method includes securing an inner strap of a belt portion of the lumbar-supporting back-bracing apparatus around a torso and a low back of the user, thereby securing the apparatus around the torso of the user. The method includes securing an upper outer strap of the belt portion around around the inner strap, the torso and the low back of the user. The upper outer strap is configured to pass through the first and second upper slots of the at least one rib of the plurality of posterior ribs. The method includes securing a lower outer strap of the belt portion around the inner strap, the torso and the low back of the user. The lower outer strap is configured to pass through the first and second lower slots of the at least one rib of the plurality of posterior ribs.

BRIEF DESCRIPTION OF THE DRAWINGS

While the appended claims set forth the features of the present techniques with particularity, these techniques, together with their objects and advantages, may be best understood from the following detailed description taken in conjunction with the accompanying drawings.

FIG. 13 illustrates a method of manufacturing a lumbar-supporting back-bracing apparatus, in accordance with some example embodiments.

DETAILED DESCRIPTION OF EXEMPLARY EMBODIMENTS

Figure 1:
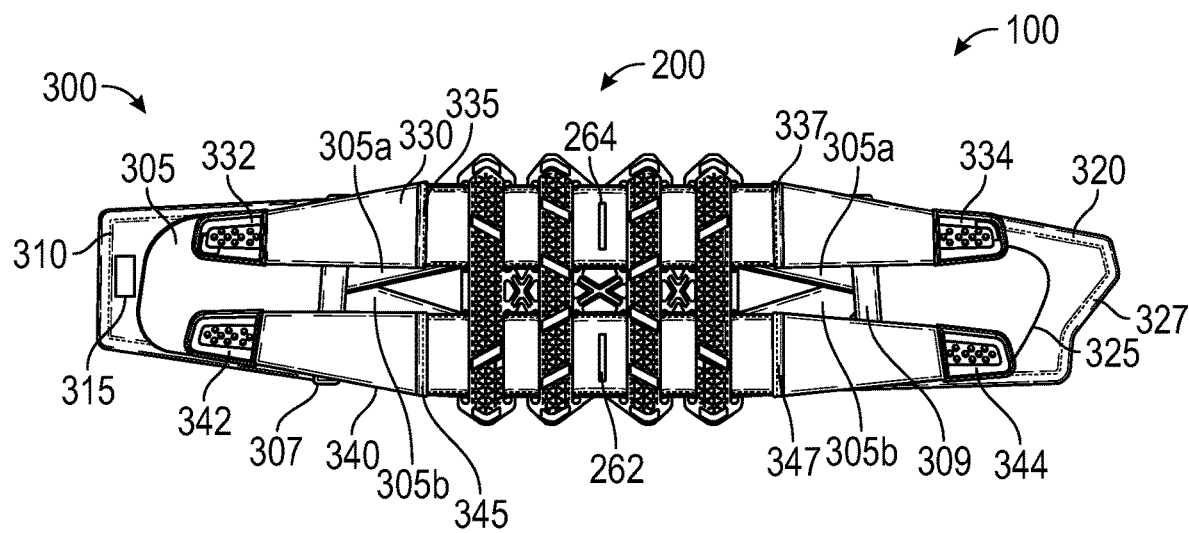
FIG. 1 illustrates a front view of a lumbar-supporting back-bracing apparatus, in accordance with some example embodiments.

Turning to the drawings, wherein like reference numerals refer to like elements, techniques of the present disclosure are illustrated as being implemented in a suitable environment. The following description is based on embodiments of the claims and should not be taken as limiting the claims with regard to alternative embodiments that are not explicitly described herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The word "orthosis" or "orthotic" is used herein to mean a brace or other such device. Consequently, orthosis may be used interchangeably with the term "brace" and may refer to specific types of braces when indicated (e.g., a back apparatus, a back orthosis and/or a back brace).

A better understanding of the various features of the disclosure can be gleaned from the following description read in conjunction with the accompanying drawings. While the disclosure may be susceptible to various modifications and alternative constructions, certain illustrative features are shown in the drawings and are described in detail below. It will be understood, however, that there is no intention to limit the disclosure to the specific embodiments disclosed, but to the contrary, the intention is to cover all modifications, alternative constructions, combinations, and equivalents falling within the spirit and scope of the disclosure.

Furthermore, it will be appreciated that unless a term is expressly defined in this disclosure to possess a described meaning, there is no intent to limit the meaning of such term, either expressly or indirectly, beyond its plain or ordinary meaning.

For ease of understanding the disclosed features of an orthopedic device, as used herein, "proximal" has its ordinary meaning and refers to a location situated next to or near the point of attachment or origin or a central point or located toward the center of the body. Likewise, the term "distal" has its ordinary meaning and refers to a location that is situated away from the point of attachment or origin or central point or located away from the center of the body. The term "medial" refers to a position that is closer to the midline of the body, whereas the term "lateral" refers to a position further from the midline of the body. The terms "upper" and "lower" describe the position of certain elements as being either above or below one or more other elements. The term "posterior" also has its ordinary meaning and refers to a location that is behind or to the rear of another location or feature. Lastly, the term "anterior" has its ordinary meaning and refers to a location that is ahead of or to the front of another location or feature.

The terms "rigid," "flexible," "malleable" and "resilient" may be used herein to distinguish portions of certain features of an apparatus. The term "rigid" is intended to mean an element of the apparatus is generally or substantially inflexible. Within the context of frame or support members or shells that are "rigid," it is intended to indicate that they do not lose their overall shape when force is applied. The term "flexible" or "malleable", by contrast, is intended to encompass features that are capable of bending or flexing under load.

The present disclosure contemplates one or more lumbar-supporting, back-bracing apparatuses and associated methods of use and/or manufacture. Such apparatuses can provide pain relief for acute or chronic low back pain for active users at least partially through their restraining effect and distribution of physical load along, over and/or across the vertebral discs, improvement of postural control with limitation of extreme amplitudes and proprioceptive reminders, increased user mobility which promotes the resumption of physical activity, functional rehabilitation, social and/or professional integration, and improvement of muscle tone through strengthening of the strap abdominal and flexor muscles of the trunk.

Such apparatuses can be self-prescribed or prescribed by any suitable professional including but not limited to a general practitioner, sports or occupational physician, physiotherapist, physical therapist, masseuse and/or a clinic, and may be made available from any appropriate retail or wholesale store such as pharmacies and/or medical stores.

In some embodiments, such apparatuses provide a unique combination of high quality, sleek technical design that utilizes less fabric or textile than conventional devices and, thereby, provides a more breathable feel, increased durability under use, and increased elasticity. In addition to features otherwise described in this disclosure, such apparatuses may also benefit from manufacturing innovations including but not limited to CarpaForm™ and RhizoForm™ as well as, or in addition to, other advantages afforded and/or otherwise provided by the comfort and elasticity of the PoroStrap™, maintenance of shape and form via boning such as ActiStrap™ and/or ease of strap adjustment provided by quadruple booster straps such as ImmoStrap™.

Ideal for extreme conditions, impact resistance and moderate to heavy immobilization, active people and/or those who work outside and who are exposed to significant risk of developing back pain may benefit greatly from the improved, novel and inventive designs described throughout this disclosure.

Discussion of one or more embodiments of a lumbar-supporting and/or back-bracing apparatus according to the disclosure will now be discussed below in connection with one or more figures.

Figure 2:
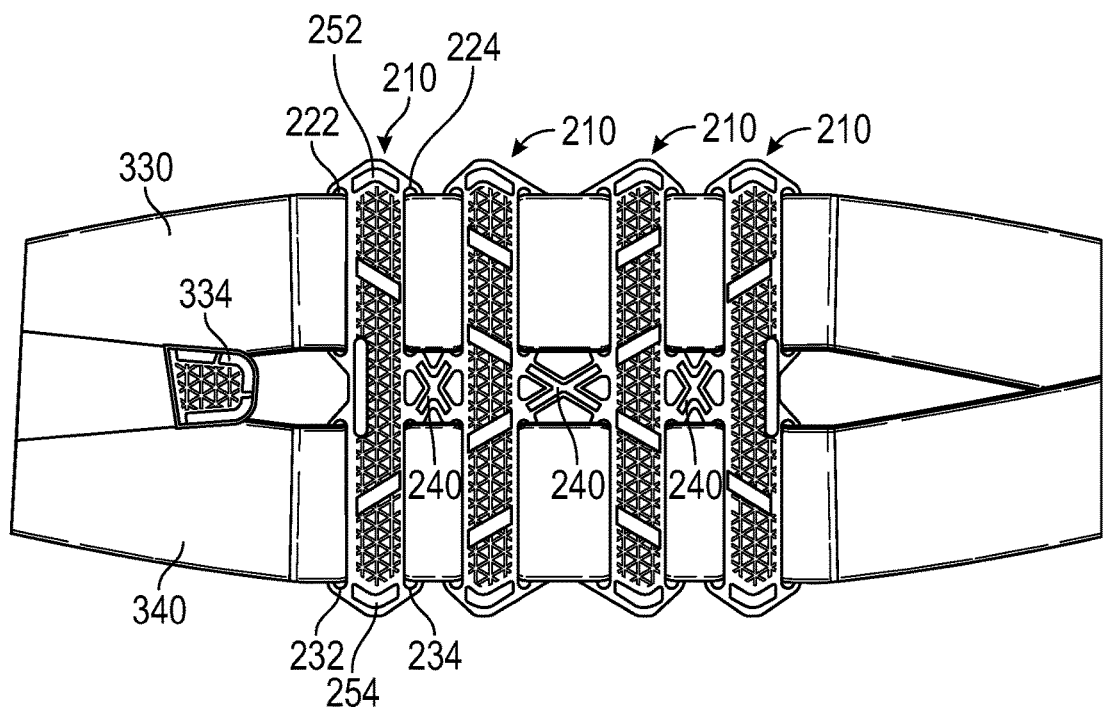
FIG. 2 illustrates a magnified front view of a portion of the apparatus of FIG. 1, in accordance with some example embodiments.
Figure 8:
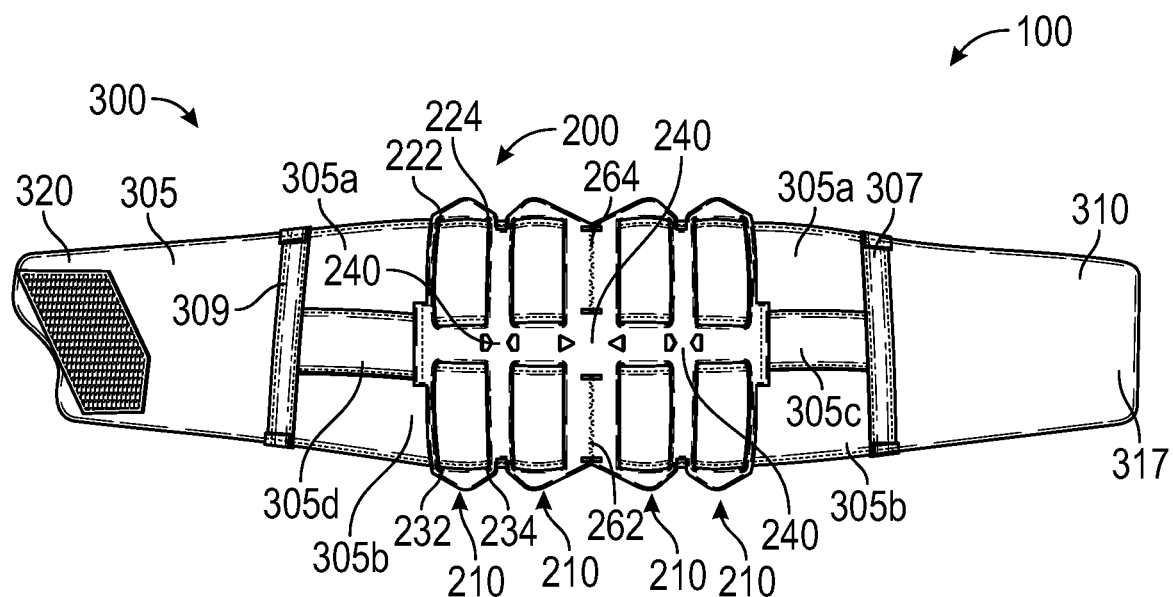
FIG. 8 illustrates a back view of a lumbar-supporting back-bracing apparatus, in accordance with some example embodiments.
Figure 9:
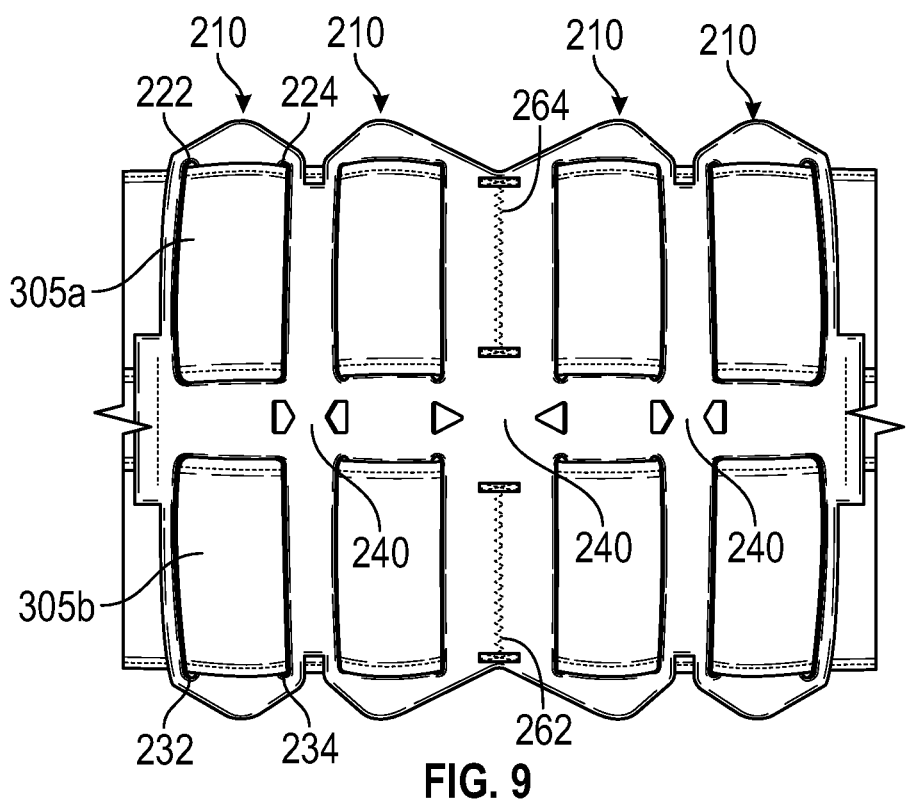
FIG. 9 illustrates a magnified back view of a central portion of the apparatus of FIG. 9, in accordance with some example embodiments.
Figure 10:
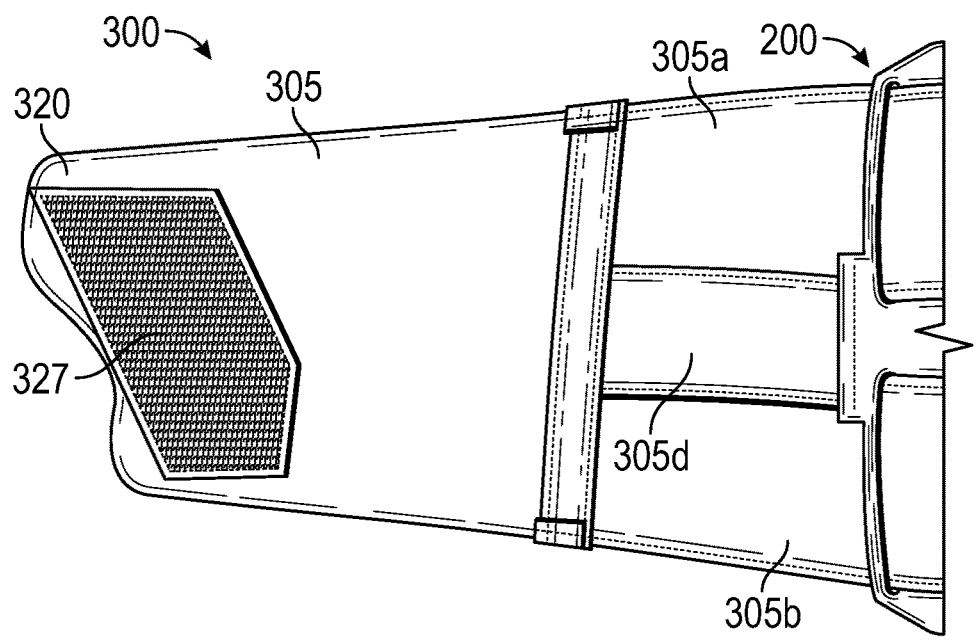
FIG. 10 illustrates a magnified back view of a first lateral portion of the apparatus of FIG. 9, in accordance with some example embodiments.
Figure 11:
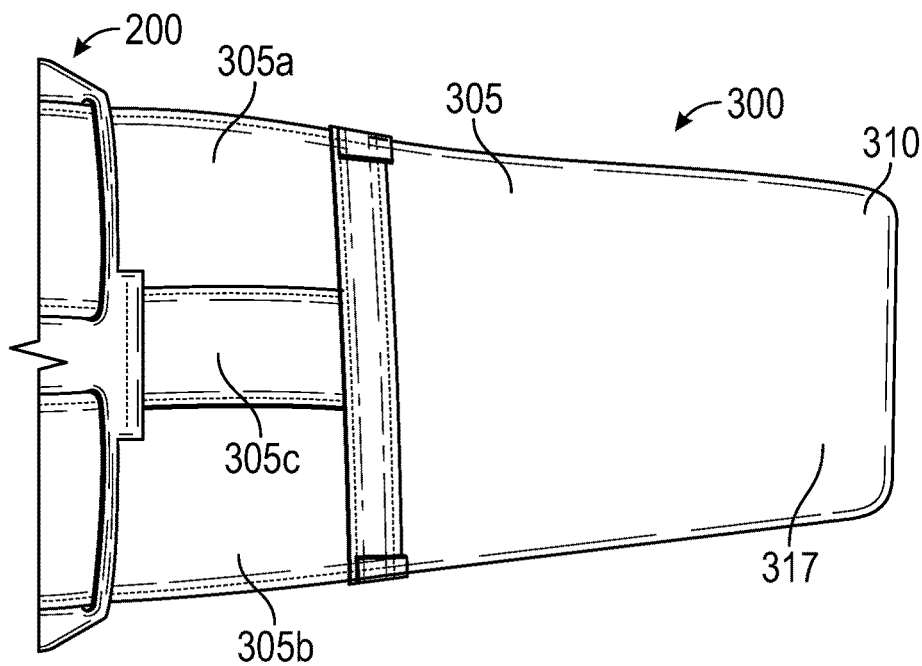
FIG. 11 illustrates a magnified back view of a second lateral portion of the apparatus of FIG. 9, in accordance with some example embodiments.

FIG. 1 illustrates a front view of a lumbar-supporting back-bracing apparatus 100, while FIG. 2 illustrates a magnified front view of a portion of apparatus 100 of FIG. 1, in accordance with some example embodiments. FIG. 8 illustrates a back view of lumbar-supporting back-bracing apparatus 100, while FIGS. 9-12 illustrate magnified back, front or substantially cross-sectional views of different portions of apparatus 100, in accordance with some embodiments. Lumbar-supporting back-bracing apparatus 100 can comprise a support portion 200 and a belt portion 300. In some embodiments, support portion 200 comprises a plurality of posterior ribs 210 configured to abut and extend vertically along a lumbar portion of user's lower back. Posterior ribs 210 may be rigid or semi-rigid but, in some embodiments, at least partially conformable to the anatomy of the user's lower back. While the present disclosure contemplates any number of posterior ribs 210, at least FIGS. 1, 2, 8 and 9 illustrate four posterior ribs laterally spaced from one another. In some embodiments, each of posterior ribs 210 is laterally spaced from an adjacent rib by a same distance. In some other embodiments, posterior ribs 210 are laterally spaced from adjacent rib(s) by one or more different distances. In some embodiments, each of posterior ribs 210 can have a same length, for example, 21 centimeters or 26 centimeters. However, the present disclosure is not so limited and contemplates posterior ribs 210 of any same or varied suitable length(s).

Each of posterior ribs 210 can comprise a first upper slot 222 and a second upper slot 224 disposed on either side of an upper portion of the respective posterior rib 210. First and second upper slots 222, 224 are configured to receive one or more straps of belt portion 300 to thereby secure the apparatus 100 against a low back and torso of the user. Each of posterior ribs 210 can also comprise a first lower slot 232 and a second lower slot 234 disposed on either side of a lower portion of the respective posterior rib 210. First and second lower slots 232, 234 are configured to receive one or more straps of belt portion 300 to thereby secure the apparatus 100 against a low back and torso of the user. In some embodiments, one or more of posterior ribs 210 can have at least a first indicator 252 disposed at one end of the posterior rib(s) and, optionally, a second indicator 254 disposed at a second end of the posterior rib(s). First and/or second indicators 252, 254 can identify the top and/or bottom ends, respectively, of apparatus 100 and may aid the user in assembling and/or putting on apparatus 100 in the proper orientation. One or more aspects and/or features of first and/or second indicators 252, 254 will be described in more detail below, in connection with one or more other features of support portion 200.

Posterior ribs 210 are coupled to one another via a bracing web component 240 comprising a plurality of crossing and/or x-shaped structures. In some embodiments, as illustrated in FIGS. 1, 2, 8 and 9, each posterior rib 210 is coupled to an adjacent posterior rib via one such crossing and/or x-shaped structure of bracing web component 240. Such crossing and/or x-shaped structures provide damping of vibrations through apparatus 100 and thereby protection for the low back of the user.

Figure 12:
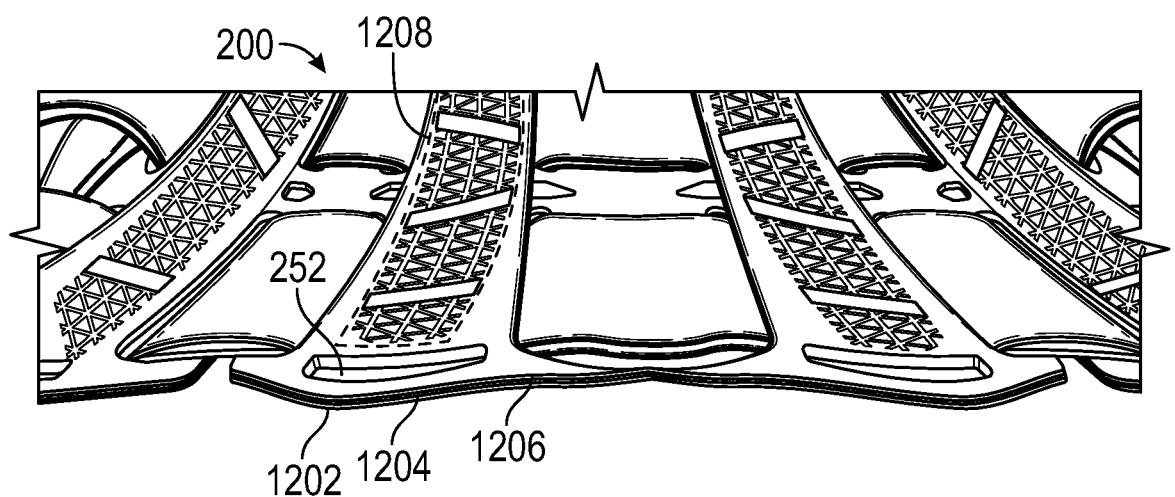
FIG. 12 illustrates a magnified, substantially cross-sectional view of a support portion of a lumbar-supporting back-bracing apparatus comprising sandwiched layers, in accordance with some example embodiments.

In some embodiments, any of posterior ribs 210, slots 222, 224, 232, 234, and bracing web component 240, individually or formed together as an integral piece, can comprise a layered structure, as illustrated in more detail in at least FIG. 12. In some embodiments, such a layered structure can comprise stiffening steel, metal or otherwise rigid but conformable stays 1208 sandwiched between an outer layer 1206 comprising, for example, polyurethane overinjected onto textile and an inner layer 1202 comprising, for example, a soft, absorbent material, such as cloth, foam, etc. However, the present application is not so limited and outer layer 1206 and/or inner layer 1202 may comprise any respective suitable material(s). Moreover, while an example stay 1208 is illustrated in FIG. 12 for ease of reference, it should be understood that any number of stays can be disposed between inner layer 1202 and outer layer 1206 and such stays may have any suitable shape(s) to form any portion of ribs 210, slots 222, 224, 232, 234 and/or crossing and/or x-shaped structure of bracing web component 240 as described anywhere herein.

Outer layer 1206 may provide external protection and durability for apparatus 100. Inner layer 1202 may provide added comfort to the user, both in terms of padding and ability to wick moisture away from the user's torso and/or low back. And the stiffening stays 1208 may provide rigid but at least partially conformal support for the low back of the user. In some embodiments, the stiffening stays 1208 are disposed within posterior ribs 210 of support portion 200. In some embodiments, the stiffening stays 1208 are also disposed in at least a portion of material defining one or more of slots 222, 224, 232, 234, for example along a perimeter of one or more of slots 222, 224, 232, 234. In some embodiments, the stiffening stays 1208 also define at least a portion of bracing web component 240, for example forming at least a portion of the plurality of crossing and/or x-shaped structures to improve rigidity and/or the torsion-withstanding ability of bracing web component 240 compared to embodiments not having such stiffening stays disposed within bracing web component 240.

In some embodiments, the stiffening stays 1208 may be secured between inner layer 1202 and outer layer 1206 utilizing any suitable process, for example, a thermo-compressing process in which an adhesive is applied to facing sides of inner layer 1202 and outer layer 1206 and activated by heat and/or pressure by pressing the layers together with sufficient force and/or heat.

In some embodiments, at least one of first and second indicators 252, 254 can be formed from an indicator layer 1204 disposed between inner layer 1202 and outer layer 1206 before the multiple layers are secured to one another, as otherwise described above. In some embodiments, indicator layer 1204 comprises a fabric, plastic or any other suitable material having a color and/or texture different from one or both of inner layer 1202 and outer layer 1206 such that, when rendered visible to a user, indicator layer 1204 is readily identifiable at first and/or second indicators 252, 254 for at least an orientation-indicating purpose. In some such embodiments, adhesive may be similarly applied to at least a portion of one or both sides of indicator layer 1206 before it is disposed between inner layer 1202 and outer layer 1206.

Once inner layer 1202, outer layer 1206, the stays 1208 and, in some embodiments also indicator layer 1204, are bonded to one another, a die cutting operation may be utilized to cut away excess portions of inner and outer layers 1202, 1206 and, in some embodiments also indicator layer 1204, to thereby realize at least the crossing and/or x-shaped structure of bracing web component 240. In some embodiments, such a die cutting operation can also be utilized to cut away excess portions of inner and outer layers 1202, 1206 in the same operation to form indicator(s) 252 and/or 254, once exposed through a window in at least outer layer 1206. For example, where indicator layer 1204 is utilized, at least a portion of outer layer 1206 can be cut away to, thereby, expose a portion of indicator layer 1204 at the location(s) of one or both of first and second indicators 252, 254. Utilizing indicator layer 1204 as opposed to a conventional sticker or marker functioning as an indicator allows formation of indicators 252, 254 in fewer steps, since a die cutting operation that defines one or more sections of support portion 200 can also be utilized to remove the portion of outer layer 1206 and exposing the portion(s) of indicator layer 1204 at one or both of indicators 252, 254 in the same operation. In some embodiments, such a die cutting operation can also be utilized to cut away excess portions of at least inner and outer layers 1202, 1206 in the same operation to form posterior ribs 210 including the first and second upper and lower slots 222, 224, 232, 234. In some embodiments, one or more portions of the apparatus elastics (e.g., one or more parts of belt portion 300) can also be assembled and/or formed at outer layer 1206 during such a sandwich-bonding process.

Discussion now turns to belt portion 300 of apparatus 100. As illustrated in at least FIGS. 1, 2 and 8-12, belt portion 300 can comprise an inner strap 305. Inner strap 305 is configured as the inner-most belt layer to be wrapped around the torso and lower back of the user. Inner strap 305 can comprise a first end 310 and a second end 320. In some embodiments, inner strap 305 splits at a first seam 307, from a unitary piece near first end 310 into an upper portion 305*a* and a lower portion 305*b*, each configured to pass respectively through the upper slots 222, 224 and lower slots 232, 234 of one or more of posterior ribs 210 of support portion 200. Upper and lower portions 305*a*, 305*b* of inner strap 305 can then merge back into a unitary piece at a second seam 309, beyond the upper and lower slots of posterior ribs 210, near second end 320. In some embodiments, as illustrated in at least FIGS. 8-11, inner strap 305 can further comprise a first central portion 305*c* coupled to and extending medially from a central portion of first seam 307 to a central portion of an adjacent side of support portion 200. Similarly, in some embodiments, as illustrated in at least FIGS. 8-11, inner strap 305 can further comprise a second central portion 305*d* coupled to and extending medially from a central portion of second seam 309 to a central portion of an adjacent side of support portion 200. As illustrated in FIG. 8, first and second central portions 305*c*. 305*d* can be disposed at a backside of one or both of upper and lower inner straps 305*a*, 305*b*. However, the present disclosure is not so limited and first and second central portions 305*c*, 305*d* can be disposed at a frontside of one or both of upper and lower inner straps 305*a*. 305*b*. In some embodiments, first and second central portions 305c, 305d can provide direct anchors of inner strap 305 to support portion 200 and, thereby provide additional aid in properly alignment of support portion 200 with respect to the user's lower back and/or torso and/or with respect to inner strap 305.

Figure 7:
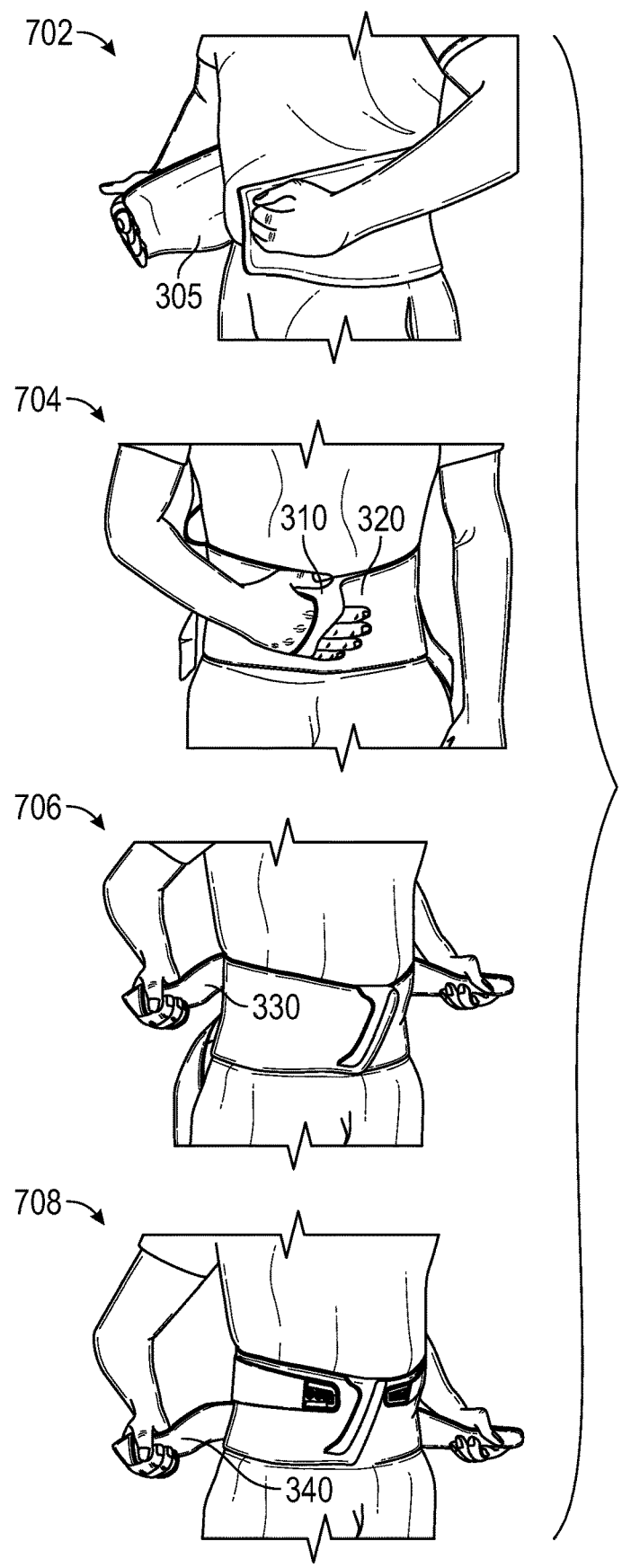
FIG. 7 illustrates a method of securing a lumbar-supporting back-bracing apparatus to a user, in accordance with some example embodiments.

In some embodiments, first and second ends 310, 320 of inner strap 305 can further comprise respective fasteners 317, 327 such as hook and loop fasteners or any other suitable fastener. In some embodiments, first end 310 further comprises a first pocket or loop 315 and second end 320 comprises a second pocket or loop 325 configured such that a user can hold onto these pockets or loops 315, 325 with either hand as he or she pulls inner strap 305 tightly around his or her torso and low back and brings fastener(s) 317 of first end 310 into physical contact with fastener(s) 327 of second end 320, thereby allowing for an appropriately snug securement of inner strap 305 around the torso and low back of the user. This pulling and wrapping of inner strap 305 around the torso and low back of the user is illustrated in at least illustration 702 of FIG. 7, while the overlapping and fastening of first end 310 and second end 320 of inner belt 305 is illustrated in at least illustration 704 of FIG. 7.

In some embodiments, belt portion 300 also comprises at least one outer strap 330, 340. For example, at least FIGS. 1 and 2 illustrate an upper outer strap 330 and a lower outer strap 340. Upper outer strap 330 and lower outer strap 340 are each configured as an outer-most belt layer to be wrapped around the torso and lower back of the user and around inner strap 305.

Figure 3:
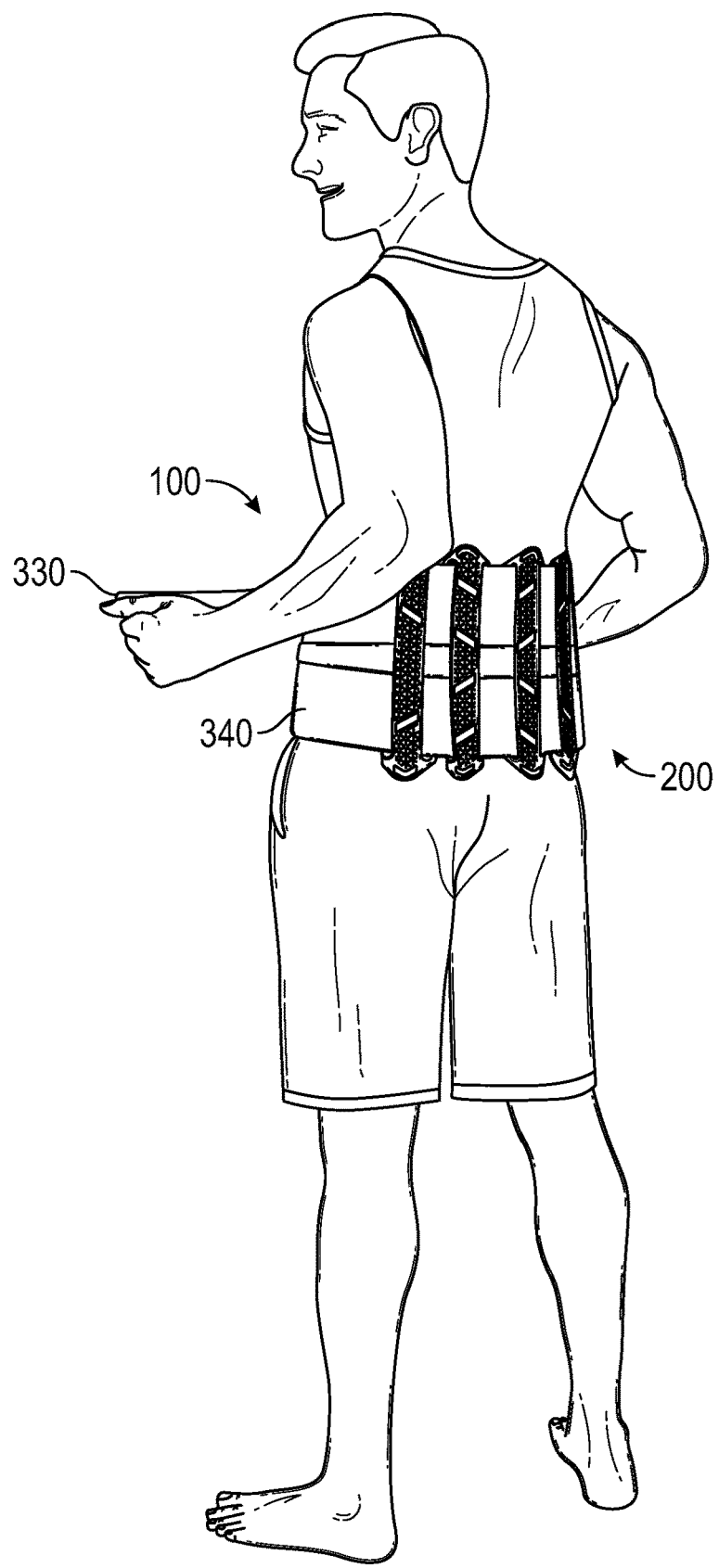
FIG. 3 illustrates a lumbar-supporting back-bracing apparatus being worn by a user, in accordance with some example embodiments.

Upper outer strap 330 is configured to pass through the upper slots 222, 224 of one or more of posterior ribs 210 of support portion 200 and, in some cases, over the upper portion of inner strap 305 as it does so. In some embodiments, upper outer strap 330 is sewn or otherwise bonded to at least a portion of the upper portion of inner strap 305, for example at a first seam 335 disposed near and to a same side of support portion 200 as a first end 332 of upper inner strap 305a, at a second seam 337 disposed near and to a same side of support portion 200 as a second end 334 of upper inner strap 305a, and/or at a central seam 264 disposed substantially at a centerline of support portion 200. In some embodiments, central seam 264 may sew or otherwise bond both upper outer strap 330 and inner upper strap 305a to the support portion 200 of apparatus 200 substantially at the centerline of support portion 200. Accordingly, in some such embodiments, central seam 264 may extend through to and along the backside of support portion 200 as illustrated in at least FIGS. 8 and 9. In some other embodiments, upper outer strap 330 is separate from and not sewn or otherwise permanently bonded to the upper portion of inner strap 305. In some embodiments, first and second ends 332, 334 of upper outer strap 330 can each further comprise fasteners, similar to inner strap 305, such as hook and loop fasteners or any other suitable type of fasteners. In some embodiments, a user can hold onto first and second ends 332, 334 with either hand as he or she pulls upper outer strap 330 tightly around his or her torso, low back and inner strap 305 and fastens the fastener(s) of first end 332 to one of inner strap 305 or second end 334, thereby allowing for an appropriately snug securement of upper outer strap 330 around the torso and low back of the user. In some embodiments, at least one of upper outer strap 330, its first end 332 or its second end 334 can further comprise an indicator, similar to or different from indicator 252 of support portion 200 of apparatus 100, to identify upper outer strap 330 as the outer strap that extends through upper slots 222, 224 of posterior ribs 210 and aid the user in putting apparatus 100 on in the proper orientation. This pulling, wrapping and securing of upper outer strap 330 is illustrated in at least FIG. 3 and illustration 706 of FIG. 7.

Figure 4:
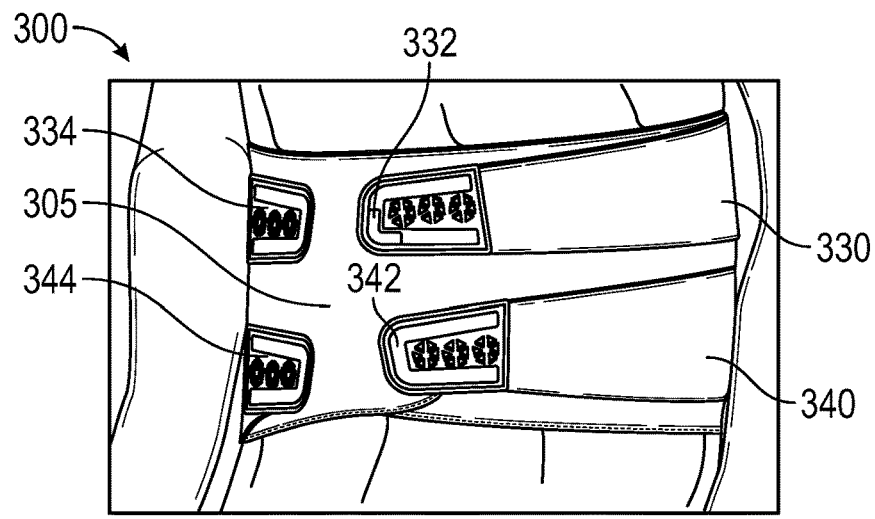
FIG. 4 illustrates a magnified front view of the apparatus of FIG. 3 being worn by a user, in accordance with some example embodiments.
Figure 5:
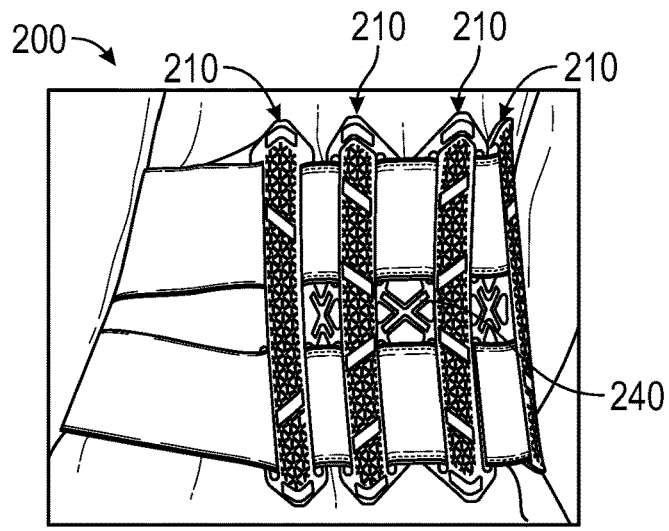
FIG. 5 illustrates a magnified rear view of the apparatus of FIG. 3 being worn by a user, in accordance with some example embodiments.
Figure 6:
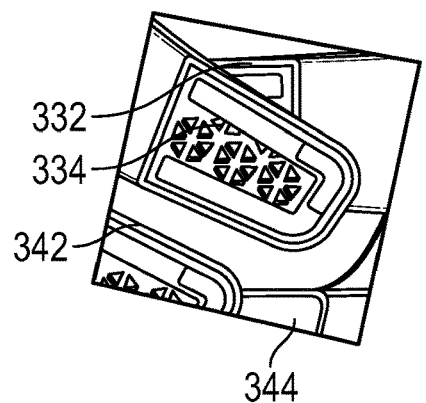
FIG. 6 illustrates a magnified view of one or more fasteners of the apparatus of FIG. 3 being worn by a user, in accordance with some example embodiments.

Lower outer strap 340 is configured to pass through the lower slots 232, 234 of one or more of posterior ribs 210 of support portion 200 and, in some cases, over the lower portion of inner strap 305 as it does so. In some embodiments, lower outer strap 340 is sewn or otherwise bonded to at least a portion of the lower portion of inner strap 305, for example at a first seam 345 disposed near and to a same side of support portion 200 as a first end 342 of lower inner strap 305b, at a second seam 347 disposed near and to a same side of support portion 200 as a second end 334 of upper inner strap 305b, and/or at a central seam 262 disposed substantially at a centerline of support portion 200. In some embodiments, central seam 262 may sew or otherwise bond both lower outer strap 340 and inner lower strap 305b to the support portion 200 of apparatus 200 substantially at the centerline of support portion 200. Accordingly, in some such embodiments, central seam 262 may extend to and along the backside of support portion 200 as illustrated in at least FIGS. 9 and 10. In some other embodiments, lower outer strap 340 is separate from and not sewn or otherwise permanently bonded to the lower portion of inner strap 305. In some embodiments, first and second ends 342, 344 of lower outer strap 340 can each further comprise fasteners, similar to inner strap 305, such as hook and loop fasteners or any other suitable type of fasteners. In some embodiments, a user can hold onto first and second ends 342, 344 with either hand as he or she pulls lower outer strap 340 tightly around his or her torso, low back and inner strap 305 and fastens the fastener(s) of first end 342 to one of inner strap 305 or second end 344, thereby allowing for an appropriately snug securement of lower outer strap 340 around the torso and low back of the user. In some embodiments, at least one of lower outer strap 340, its first end 342 or its second end 344 can further comprise an indicator, similar to, or different from, indicator 254 of support portion 200 of apparatus 100, to identify lower outer strap 340 as the outer strap that extends through lower slots 232, 234 of posterior ribs 210 and aid the user in putting apparatus 100 on in the proper orientation. This pulling, wrapping and securing of lower outer strap 340 is illustrated in at least illustration 708 of FIG. 7. FIG. 4 illustrates an anterior view of the apparatus 100 with belt portion 300 secured around the torso of the user and first and second ends 332, 334 of upper outer strap 330 and first and second ends 342, 344 of lower outer strap 340 each secured to a portion of already-secured inner strap 305. FIG. 5 illustrates a posterior view of apparatus 100 with support portion 200 secured against the low back of the user. FIG. 6 illustrates a magnified view of an embodiment in which first and second ends 332, 334 of upper outer strap 330 overlap and are at least partially secured to one another and in which first and second ends 342, 344 of lower outer strap 340 overlap and are at least partially secured to one another, rather than or in addition to being at least partially secured to a portion of already-secured inner strap 305.

Inner strap 305 (including, for example, upper, lower and central portions 305a-305d), upper outer strap 330 and lower outer strap 340 are easy to clean and maintain and provide better low back support for a user of apparatus 100 compared to conventional back brace designs. In some embodiments, one or more of inner strap 305, upper outer strap 330 and lower outer strap 340 can comprise antimicrobial, anti-odor, thermoregulatory and/or hypoallergenic "on steam" materials. In some embodiments, one or more of inner strap 305, upper outer strap 330 and lower outer strap 340 can comprise a honeycomb design such as Artico™ fabric. In some embodiments, one or more of inner strap 305, upper outer strap 330 and lower outer strap 340 can be formed in such a way so as not to have stitched external borders to provided better comfort for the user compared to conventional back brace designs in which stitched external borders might otherwise dig into and/or otherwise create uncomfortable pressure points on the torso of the user.

In some embodiments, one or more of inner strap 305, upper outer strap 330 and lower outer strap 340 can be fabricated or made available in one or more of a plurality of sizes. For example and not limitation, extra small (XS) for an example waist size of 56-68 cm, small (S) for an example waist size of 68-82 cm, medium (M) for an example waist size of 82-98 cm, large (L) for an example waist size of 98-116 cm and extra large (XL) for an example waist size of 116-136 cm.

Discussion will now turn to an example method of manufacturing a lumbar-supporting back-bracing apparatus, such as that described in connection with any of FIGS. 1-12. FIG. 13 illustrates a flowchart 1300 corresponding to such a method of manufacturing a lumbar-supporting back-bracing apparatus, in accordance with some example embodiments.

Block 1302 includes forming a support portion of a lumbar-supporting, back-bracing apparatus. An example includes apparatus 100 as previously discussed in connection with FIGS. 1-12. This forming the support portion can be carried out as described in connection with at least blocks 1304 and 1306 below and/or as previously described in connection with any figure herein.

Block 1304 includes forming a plurality of posterior ribs configured to abut and extend along a low back of a user by sandwiching rigid metallic stays between an outer layer comprising polyurethane overinjected onto textile and an inner layer comprising a soft, absorbant material. For example, as previously described in connection with at least FIGS. 1, 2 and 8-12, rigid metallic stays 1208 can be sandwiched between outer layer 1206 comprising, for example, polyurethane overinjected onto textile and inner layer 1202 comprising, for example, a soft, absorbant material. In further example, at least one of posterior ribs 210 comprises first upper slot 222 disposed at a first upper side of the rib and second upper slot 224 disposed at a second upper side of rib 210 opposite the first upper side, and first lower slot 232 disposed at a first lower side of rib 210 and second lower slot 234 disposed at a second lower side of rib 210 opposite the first lower side. In some embodiments, the ribs 210 are rigid yet at least partially conformable to the low back of the user. In some embodiments, ribs 210 are laterally spaced from adjacent ribs by a same distance. In some embodiments, at least one of the ribs 210 is laterally spaced from an adjacent rib by a first distance and at least one other of the ribs 210 is laterally spaced from an adjacent rib by a second distance different from the first distance. In some embodiments, ribs 210 each have a same length. In some embodiments, forming support portion 200 further includes forming or otherwise providing first indicator 252 at one end of at least one of ribs 210 to indicate an orientation of apparatus 100. In some embodiments, forming or otherwise providing first indicator 252 comprises further disposing indicator layer 1204 between outer layer 1206 and inner layer 1202 and removing a portion of at least outer layer 1206, thereby exposing at least a portion of indicator layer 1204 at the end of rib(s) 210.

Block 1306 includes forming a bracing web component comprising a plurality of crossing structures from at least the outer layer and the inner layer, wherein each rib of the plurality of posterior ribs is physically coupled to an adjacent rib of the plurality of posterior ribs by at least one of the crossing structures. For example, as previously described in connection with at least FIGS. 1 and 2, the x-shaped crossing structures of bracing web component 240 can be formed from at least outer layer 1206 and inner layer 1202. Each rib 210 is physically coupled to an adjacent rib 210 by at least one of these x-shaped crossing structures. In some embodiments, each of the plurality of crossing structures of bracing web component 240 are formed as an x-shaped structure that is configured to dampen vibrations in apparatus 100. In such embodiments, each x-shaped structure can couple one of the ribs to an adjacent rib.

Block 1308 includes providing a belt portion of the lumbar-supporting, back-bracing apparatus. An example includes belt portion 300 of apparatus 100 as previously discussed in connection with FIGS. 1-12. This forming the belt portion can be carried out as described in connection with at least blocks 1310, 1312 and 1314 below.

Block 1310 includes forming an inner strap that is configured to be coupled to the support portion and to wrap around a torso and a low back of the user and thereby the apparatus to be secured around the torso of the user. For example, as previously described in connection with at least FIGS. 1, 2 and 8-12, inner strap 305 is configured to be coupled to support portion 200 and to wrap around a torso and low back of the user so the apparatus can be secured around the torso of the user. In some embodiments, forming the inner strap includes disposing first fastener 317 at first end 310 of inner strap 305 and disposing second fastener 327 at second end 320 of inner strap 305 such that when first and second ends 310, 320 overlap one another first and second fasteners 317, 327 couple to one another, thereby securing inner strap 305 around the torso of the user. In some embodiments, forming inner strap 305 further includes forming first pocket or loop 315 at first end 310 of inner strap 305 and forming second pocket or loop 325 at second end 320 of inner strap 3050, thereby providing structures for the user to grasp while securing inner strap 305 around the torso.

In some embodiments, inner strap 305 splits from a unitary piece adjacent to first end 310 into upper portion 305a configured to pass through first and second upper slots 222, 224 of ribs 210 and lower portion 305b configured to pass through first and second lower slots 232, 234 of ribs 210, upper portion 305a and lower portion 3005b merging back into a unitary piece adjacent to second end 320. In some embodiments, inner strap 305 further splits from the unitary piece adjacent to first end 310 into first central portion 305c configured to extend to and couple to a first adjacent side of support portion 200, and upper portion 305a, lower portion 305b and second central portion 305d merge back into the unitary piece adjacent to second end 320 such that second central portion 305b is configured to extend to and couple to a second adjacent side of support portion 200.

Block 1312 includes forming an upper outer strap that is configured to pass through the first and second upper slots of the at least one rib of the plurality of posterior ribs and to wrap around around the inner strap, the torso and the low back of the user. For example, as previously described in connection with at least FIGS. 1, 2 and 8-12, upper outer strap 330 is configured to pass through the first and second upper slots 222, 224 of ribs 210 and to wrap around inner strap 305, the torso and the low back of the user.

In some embodiments, forming upper outer strap 330 includes disposing a first fastener at first end 332 and disposing a second fastener at second end 334, the first and second fasteners of upper outer strap 330 configured to respectively secure first and second ends 332, 334 of upper outer strap 330 to one another and/or to inner strap 305. In some embodiments, forming upper outer strap 330 includes sewing upper outer strap 330 to at least a portion of inner strap 305.

Block 1314 includes forming a lower outer strap that is configured to pass through the first and second lower slots of the at least one rib of the plurality of posterior ribs and to wrap around the inner strap, the torso and the low back of the user. For example, as previously described in connection with at least FIGS. 1, 2 and 8-12, lower outer strap 340 is configured to pass through the first and second lower slots 232, 234 of ribs 210 and to wrap around inner strap 305, the torso and the low back of the user.

In some embodiments, forming lower outer strap 340 includes disposing a first fastener at first end 342 and disposing a second fastener at second end 344, the first and second fasteners of lower outer strap 340 configured to respectively secure first and second ends 342, 344 of lower outer strap 340 to one another and/or to inner strap 305. In some embodiments, forming lower outer strap 340 includes sewing lower outer strap 340 to at least a portion of inner strap 305.

In some embodiments, at least one of inner strap 305, upper outer strap 330 and lower outer strap 340 include at least one of an antimicrobial, an anti-odor, a thermoregulatory and/or a hypoallergenic material. In some embodiments, an external border of at least one of inner strap 305, upper outer strap 330 and lower outer strap 340 does not comprise stitching.

Figure 14:
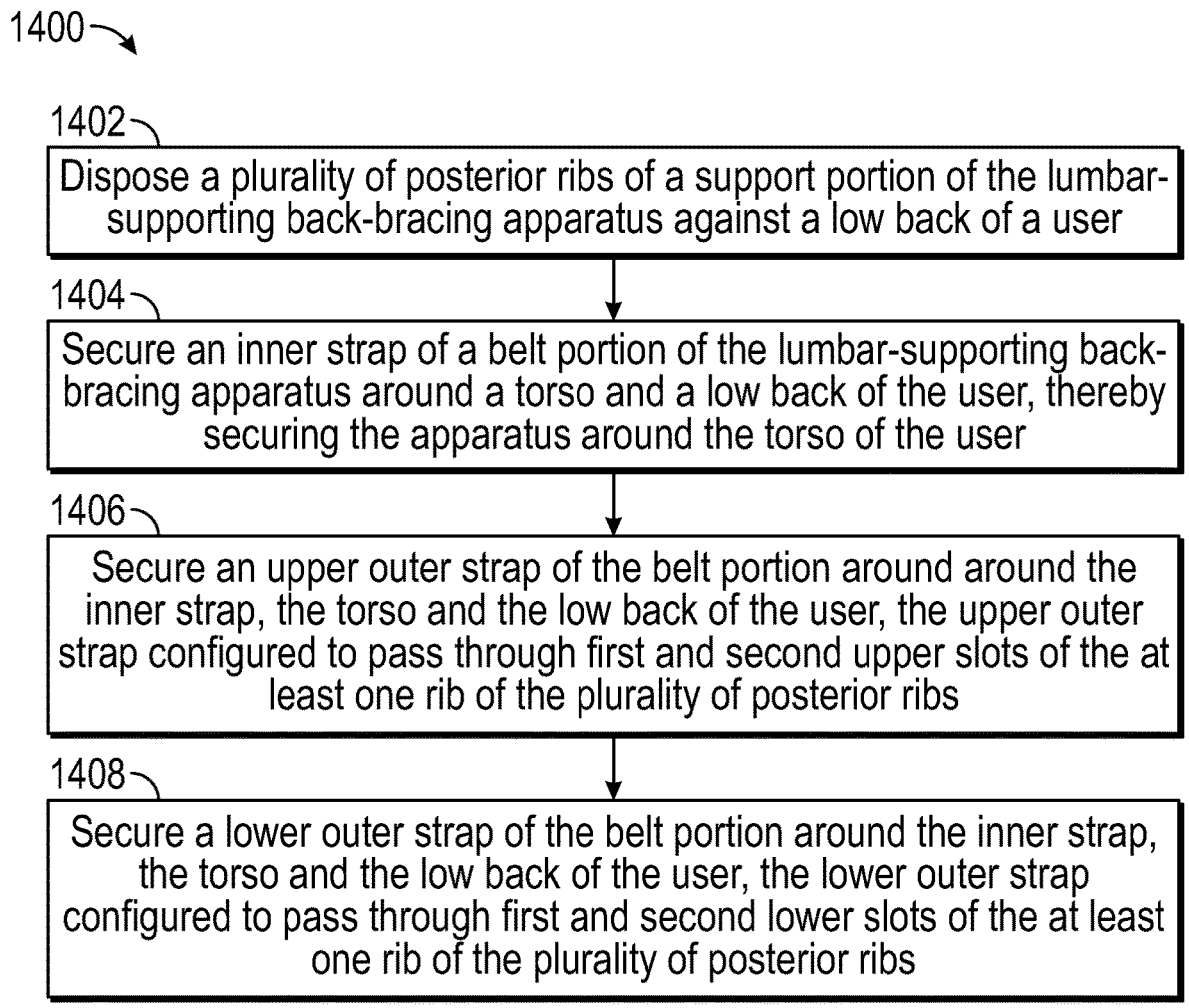
FIG. 14 illustrates a method of using a lumbar-supporting back-bracing apparatus, in accordance with some example embodiments.

Discussion will now turn to an example method of using a lumbar-supporting back-bracing apparatus, such as that described in connection with any of FIGS. 1-12. FIG. 14 illustrates a flowchart 1400 corresponding to such a method of using a lumbar-supporting back-bracing apparatus, in accordance with some example embodiments.

Block 1402 includes disposing a plurality of posterior ribs of a support portion of the lumbar-supporting back-bracing apparatus against a low back of a user. For example, a user can dispose posterior ribs 210 of support portion 200 of apparatus 100 against a low back of a user, as previously discussed in connection with at least one of FIGS. 1-12. In some embodiments, at least one of posterior ribs 210 includes a first upper slot 222 disposed at a first upper side of rib 210 and a second upper slot 224 disposed at a second upper side of rib 210 opposite the first upper side, and a first lower slot 232 disposed at a first lower side of rib 210 and a second lower slot 234 disposed at a second lower side of rib 210 opposite the first lower side. In some embodiments, support portion 200 further includes a bracing web component 240 comprising a plurality of crossing structures, each of the crossing structures physically coupling two adjacent ribs 210 of the plurality of posterior ribs.

In some embodiments, the ribs 210 are rigid yet at least partially conformable to the low back of the user. In some embodiments, ribs 210 are laterally spaced from adjacent ribs by a same distance. In some embodiments, at least one of the ribs 210 is laterally spaced from an adjacent rib by a first distance and at least one other of the ribs 210 is laterally spaced from an adjacent rib by a second distance different from the first distance. In some embodiments, ribs 210 each have a same length.

In some embodiments first indicator 252 is disposed at one end of at least one of ribs 210 to indicate an orientation of apparatus 100. In some embodiments, indicator layer 1204 is disposed between an outer layer 1206 and an inner layer 1202 and a portion of at least outer layer 1206 is removed, thereby exposing at least a portion of indicator layer 1204 at the end of rib(s) 210.

In some embodiments, each of the plurality of crossing structures of the bracing web component comprises an x-shaped structure configured to dampen vibrations in apparatus 100. In some embodiments, each x-shaped structure couples two adjacent ribs 210 of the plurality of posterior ribs. In some embodiments, at least the plurality of posterior ribs have a bonded layered structure comprising rigid metallic stays 1208 sandwiched between an outer layer 1206 comprising, for example, polyurethane overinjected onto textile, and an inner layer 1202 comprising, for example, a soft, absorbant material.

Block 1404 includes securing an inner strap of a belt portion of the lumbar-supporting back-bracing apparatus around a torso and a low back of the user, thereby securing the apparatus around the torso of the user. For example, as previously described in connection with at least one of FIGS. 1-12, a user or practicioner can secure inner strap 305 of belt portion 300 of lumbar-supporting back-bracing apparatus 100 around a torso and a low back of the user, thereby securing apparatus 100 around the torso of the user.

In some embodiments, inner strap 305 comprises a first end 310 having a first fastener 317 and a second end 320 having a second fastener 327. In some embodiments, first and second ends 310, 320 are configured to overlap one another sufficiently that first and second fasteners 317, 327 couple to one another and thereby secure inner strap 305 around the torso of the user. In some embodiments, first end 310 of inner strap 305 comprises a first pocket or loop 315 and second end 320 of inner strap 305 comprises a second pocket or loop 325. Such first and second pockets or loops 315, 325 provide structure for the user or practitioner to grasp while securing inner strap 305 around the torso of the user. In some embodiments, inner strap 305 splits from a unitary piece adjacent to first end 310 into an upper portion 305a configured to pass through first and second upper slots 222, 224 of the at least one rib 210 of the plurality of posterior ribs and a lower portion 305b configured to pass through first and second lower slots 232, 234 of the at least one rib 210 of the plurality of posterior ribs. Upper portion 305a and lower portion 305b merge back into a unitary piece adjacent to second end 320 of inner strap 305. In some embodiments, inner strap 305 further splits from the unitary piece adjacent to first end 310 into a first central portion 305c configured to extend to and couple to a first adjacent side of support portion 200. In some such embodiments, upper portion 305a, lower portion 305b and a second central portion 305d merge back into the unitary piece adjacent to second end 320 of inner strap 305. In some such embodiments, second central portion 305d is configured to extend to and couple to a second adjacent side of support portion 200.

Block 1406 includes securing an upper outer strap of the belt portion around around the inner strap, the torso and the low back of the user, the upper outer strap configured to pass through the first and second upper slots of the at least one rib of the plurality of posterior ribs. For example, as previously described in connection with at least one of FIGS. 1-12, a user or practitioner can secure upper outer strap 330 of the belt portion around around inner strap 305, the torso and the low back of the user. Upper outer strap 330 is configured to pass through first and second upper slots 222, 224 of the at least one rib 210 of the plurality of posterior ribs.

In some embodiments, upper outer strap 330 comprises a first end 332 having a first fastener and a second end 334 having a second fastener, the first and second fasteners of upper outer strap 330 configured to respectively secure first and second ends 332, 334 of upper outer strap 330 to one another and/or to inner strap 305. In some embodiments, upper outer strap 330 is sewn to at least a portion of inner strap 305.

Block 1408 includes securing a lower outer strap of the belt portion around the inner strap, the torso and the low back of the user, the lower outer strap configured to pass through the first and second lower slots of the at least one rib of the plurality of posterior ribs. For example, as previously discussed in connection with at least one of FIGS. 1-12, a user or practitioner can secure a lower outer strap 340 of belt portion 300 around inner strap 305, the torso and the low back of the user. Lower outer strap 340 is configured to pass through first and second lower slots 232, 234 of the at least one rib 210 of the plurality of posterior ribs.

In some embodiments, lower outer strap 340 comprises a first end 342 having a first fastener and a second end 344 having a second fastener. The first and second fasteners of lower outer strap 340 are configured to respectively secure first and second ends 342, 344 of lower outer strap 340 to one another and/or to inner strap 305. In some embodiments, lower outer strap 340 is sewn to at least a portion of inner strap 305. In some embodiments, an external border of at least one of inner strap 305, upper outer strap 330 and lower outer strap 340 does not comprise stitching.

Reference throughout this disclosure to "an embodiment" or "the embodiment" means that a particular feature, structure or characteristic described in connection with that embodiment is included in at least one embodiment. Thus, the quoted phrases, or variations thereof, as recited throughout this disclosure are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A lumbar-supporting back-bracing apparatus, the apparatus comprising:
 a support portion comprising:
  a plurality of posterior ribs configured to abut and extend along a low back of a user, each of the plurality of posterior ribs comprising:
   a first upper slot disposed at a first upper side of the rib and a second upper slot disposed at a second upper side of the rib opposite the first upper side, and
   a first lower slot disposed at a first lower side of the rib and a second lower slot disposed at a second lower side of the rib opposite the first lower side, and
  a bracing web component comprising a plurality of rigid x-shaped crossing structures, wherein each rib of the plurality of posterior ribs is physically coupled to an adjacent rib of the plurality of posterior ribs by a respective one of the rigid x-shaped crossing structures, thereby dampening vibrations in the apparatus; and
 a belt portion comprising:
  an inner strap coupled to the support portion and configured to wrap around a torso and a low back of the user and thereby secure the apparatus around the torso of the user,
  an upper outer strap configured to pass through the first and second upper slots of each rib of the plurality of posterior ribs and wrap around the inner strap, the torso and the low back of the user, and
  a lower outer strap configured to pass through the first and second lower slots of each rib of the plurality of posterior ribs and wrap around the inner strap, the torso and the low back of the user.

2. The apparatus of claim 1, wherein the inner strap comprises a first end having a first fastener and a second end having a second fastener, the first and second ends configured to overlap one another sufficiently that the first and second fasteners couple to one another and thereby secure the inner strap around the torso of the user.

3. The apparatus of claim 2, wherein the inner strap splits from a unitary piece adjacent to the first end into an upper portion configured to pass through the first and second upper slots of the at least one rib of the plurality of posterior ribs and a lower portion configured to pass through the first and second lower slots of the at least one rib of the plurality of posterior ribs, the upper portion and the lower portion merging back into a unitary piece adjacent to the second end.

4. The apparatus of claim 3, wherein:
 the inner strap further splits from the unitary piece adjacent to the first end into a first central portion configured to extend to and couple to a first adjacent side of the support portion; and
 the upper portion, the lower portion and a second central portion merge back into the unitary piece adjacent to the second end, the second central portion being configured to extend to and couple to a second adjacent side of the support portion.

5. The apparatus of claim 2, wherein the first end of the inner strap comprises a first pocket or loop and the second end of the inner strap comprises a second pocket or loop, the first and second pockets or loops providing structure for the user to grasp while securing the inner strap around the torso.

6. The apparatus of claim 1, wherein the plurality of posterior ribs are rigid yet at least partially conformable to the low back of the user.

7. The apparatus of claim 1, wherein each rib of the plurality of ribs is laterally spaced from an adjacent rib of the plurality of ribs by a same distance.

8. The apparatus of claim 1, wherein at least one rib of the plurality of ribs is laterally spaced from an adjacent rib of the plurality of ribs by a first distance and at least one other rib of the plurality of ribs is laterally spaced from an adjacent rib of the plurality of ribs by a second distance different from the first distance.

9. The apparatus of claim 1, wherein at least one rib of the plurality of ribs comprises a first indicator disposed at one end of the rib and configured to indicate an orientation of the apparatus, the first indicator comprising an indicator layer disposed within the at least one rib of the plurality of ribs and exposed through a window in at least an outer layer of the at least one rib.

10. The apparatus of claim 1, wherein at least the plurality of posterior ribs have a bonded layered structure comprising rigid metallic stays sandwiched between an outer layer comprising polyurethane overinjected onto textile and an inner layer comprising a soft, absorbent material.

11. The apparatus of claim 1, wherein the upper outer strap comprises a first end having a first fastener and a second end having a second fastener, the first and second fasteners of the upper outer strap configured to respectively secure the first and second ends of the upper outer strap to one another and/or to the inner strap.

12. The apparatus of claim 1, wherein at least one of the upper outer strap and the lower outer strap is sewn to at least a portion of the inner strap.

13. The apparatus of claim 1, wherein the lower outer strap comprises a first end having a first fastener and a second end having a second fastener, the first and second fasteners of the lower outer strap being configured to respectively secure the first and second ends of the lower outer strap to one another and/or to the inner strap.

14. The apparatus of claim 1, wherein an external border of at least one of the inner strap, the upper outer strap and the lower outer strap does not comprise stitching.

15. A method of manufacturing a lumbar-supporting back-bracing apparatus, the method comprising:
forming a support portion by:
forming a plurality of posterior ribs configured to abut and extend along a low back of a user by sandwiching rigid metallic stays between an outer layer comprising polyurethane overinjected onto textile and an inner layer comprising a soft, absorbent material, each rib of the plurality of posterior ribs comprising:
a first upper slot disposed at a first upper side of the rib and a second upper slot disposed at a second upper side of the rib opposite the first upper side, and
a first lower slot disposed at a first lower side of the rib and a second lower slot disposed at a second lower side of the rib opposite the first lower side,
forming a bracing web component comprising a plurality of rigid x-shaped crossing structures from at least the outer layer and the inner layer, wherein each rib of the plurality of posterior ribs is physically coupled to an adjacent rib of the plurality of posterior ribs by a respective one of the rigid x-shaped crossing structures, thereby dampening vibrations in the apparatus; and
providing a belt portion by:
forming an inner strap that is configured to be coupled to the support portion and to wrap around a torso and a low back of the user and thereby the apparatus to be secured around the torso of the user,
forming an upper outer strap that is configured to pass through the first and second upper slots of each rib of the plurality of posterior ribs and to wrap around the inner strap, the torso and the low back of the user, and
forming a lower outer strap that is configured to pass through the first and second lower slots of each rib of the plurality of posterior ribs and to wrap around the inner strap, the torso and the low back of the user.

16. The method of claim 15, further comprising forming or otherwise providing a first indicator at one end of at least one rib of the plurality of ribs by disposing an indicator layer between the outer layer and the inner layer and removing a portion of the outer layer, thereby exposing at least a portion of the indicator layer at the one end of the at least one rib, the first indicator configured to indicate an orientation of the apparatus.

17. The method of claim 15, wherein each of the plurality of crossing structures of the bracing web component are formed as an x-shaped structure that is configured to dampen vibrations in the apparatus, and wherein each x-shaped structure couples one rib of the plurality of posterior ribs to an adjacent rib of the plurality of posterior ribs.

18. The method of claim 15, further comprising forming a first pocket or loop at a first end of the inner strap and forming a second pocket or loop at a second end of the inner strap, thereby providing structures for the user to grasp while securing the inner strap around the torso.

19. A method of using a lumbar-supporting back-bracing apparatus, the method comprising:
disposing a plurality of posterior ribs of a support portion of the lumbar-supporting back-bracing apparatus against a low back of a user, each rib of the plurality of posterior ribs comprising:
a first upper slot disposed at a first upper side of the rib and a second upper slot disposed at a second upper side of the rib opposite the first upper side, and
a first lower slot disposed at a first lower side of the rib and a second lower slot disposed at a second lower side of the rib opposite the first lower side,
wherein the support portion further includes a bracing web component comprising a plurality of rigid x-shaped crossing structures, each of the rigid x-shaped crossing structures physically coupling two adjacent ribs of the plurality of posterior ribs, thereby dampening vibrations in the apparatus; and
securing an inner strap of a belt portion of the lumbar-supporting back-bracing apparatus around a torso and a low back of the user, thereby securing the apparatus around the torso of the user;
securing an upper outer strap of the belt portion around the inner strap, the torso and the low back of the user, the upper outer strap configured to pass through the first and second upper slots of each rib of the plurality of posterior ribs; and
securing a lower outer strap of the belt portion around the inner strap, the torso and the low back of the user, the lower outer strap configured to pass through the first and second lower slots of each rib of the plurality of posterior ribs.

* * * * *